United States Patent
Lu

(10) Patent No.: US 10,532,957 B1
(45) Date of Patent: Jan. 14, 2020

(54) METHOD AND EQUIPMENT FOR THE PRODUCTION OF ORGANOMINERAL NANOFERTILIZERS AND OTHER TYPES OF SOLID AND LIQUID ORGANOMINERAL FERTILIZERS AND SLOW-RELEASE PESTICIDES/HERBICIDES

(71) Applicant: James Cheng-Shyong Lu, Huntington Beach, CA (US)

(72) Inventor: James Cheng-Shyong Lu, Huntington Beach, CA (US)

( * ) Notice: Subject to any disclaimer, the term of this patent is extended or adjusted under 35 U.S.C. 154(b) by 0 days.

(21) Appl. No.: 16/236,299

(22) Filed: Dec. 28, 2018

(51) Int. Cl.
 *C05F 11/02* (2006.01)
 *A01N 25/10* (2006.01)

(52) U.S. Cl.
 CPC .............. *C05F 11/02* (2013.01); *A01N 25/10* (2013.01)

(58) Field of Classification Search
 CPC .................................. C05F 11/02; A01N 25/10
 See application file for complete search history.

(56) References Cited

U.S. PATENT DOCUMENTS

| | | |
|---|---|---|
| 8,911,526 B2 | 12/2014 | Farrukh et al. |
| 9,828,299 B2 | 11/2017 | Nonomura |
| 2018/0250646 A1 | 9/2018 | Magdassi et al. |

OTHER PUBLICATIONS

Bhupinder Singh Sekhon, "Nanotechnology in agri-food production: an overview," Nanotechnol. Sci. Appl., vol. 7, pp. 31-53 (2014).
Priyanka Solanki et al., "Nanotechnologies in food and agriculture, Chap 4: Nano-fertilizers and their smart delivery system," Springer, pp. 81-101 (2015).
Steve Suppan, "Applying nanotechnology to fertilizer: rationales, research, risks and regulatory challenges," Institute for agriculture & trade policy (Oct. 2017).
A. Qureshi et al., "Nano-fertilizers: a novel way for enhancing nutrient use efficiency and crop productivity," Int. J. Curr. Microbiol. App. Sci., vol. 7(2), pp. 3325-3335 (Feb. 10, 2018).

*Primary Examiner* — Jennifer A Smith
(74) *Attorney, Agent, or Firm* — Mei & Mark LLP; Manni Li

(57) ABSTRACT

Methods and equipment to generate oxidized cellulosic nanomaterials (NMs) from natural organic materials by nanotechnological reactions and reactive oxygen species (ROS) oxidation for the coordination of nutrients to form organomineral nanofertilizers, and for the coordination of pesticides and herbicides to generate slow-release pesticide/herbicide products, as well as from organic types of waste materials by dissolution reactions, ROS oxidation and product refining processes for the coordination of nutrients and pesticides/herbicides to generate high quality solid and liquid organomineral fertilizers and slow-release pesticides/herbicides products.

9 Claims, 7 Drawing Sheets

METHOD AND EQUIPMENT FOR THE PRODUCTION OF ORGANOMINERAL NANOFERTILIZERS AND OTHER TYPES OF SOLID AND LIQUID ORGANOMINERAL FERTILIZERS AND SLOW-RELEASE PESTICIDES/HERBICIDES

BACKGROUND OF THE INVENTION

Field of the Invention

This invention is in the field of organomineral fertilizer production. This invention relates to nanotechnological process and equipment to generate nanomaterials (NMs) and reactive oxygen species (ROS) reaction processes and equipment to produce oxidized cellulosic NMs for coordination of nutrients, pesticides and herbicides to generate high quality organomineral nanofertilizers and other pesticide/herbicide nanoparticles from natural organic materials. This invention also relates to dissolution and ROS reaction processes and equipment for coordination of nutrients and pesticides and herbicides to generate high quality organomineral fertilizers from organic waste materials.

Description of the Background Art

It has been widely reported in the open literature that nanofertilizers can significantly improve crop productivity by enhancing the rate of seed germination, seedling growth, photosynthetic activity, nitrogen metabolism, and carbohydrate and protein synthesis (such as literature cited in Nanotechnology in agri-food production: an overview, Nanotech Sci Appl: 2014, 7:31-53; Nanotechnology in food and agriculture, Springer, 2015, Chap 4: 81-102; Applying nanotechnology to fertilizer, Institute for agriculture & trade policy, 2017; and Nano-fertilizers: a novel way for enhancing nutrient use efficiency and crop productivity, International J. of Current Microbiology and Applied Sciences, 2018, 7(2):3325-3335). Use of nanofertilizers also have the advantages of reducing nitrogen leaching into ground and surface water as nitrates and vaporizing into the air as nitrous oxide (nitrous oxide is about 300 times as potent as carbon dioxide causing greenhouse effects). Benefits of using nanofertilizers are advantageous in both agricultural and environmental fields.

The recent innovative ways in nanofertilizer development are mainly based on efficient use of chemical mineral nutrients and pesticides. In the nanofertilizer manufacturing and applications, nutrients or pesticides are usually processed and applied as nanoparticles (NPs) in five ways: (1) encapsulated inside porous nanomaterials (NMs), (2) absorbed or adsorbed on NMs, (3) complexed on NMs by ligands, (4) coated with a thin polymer film on NMs, or (5) delivered as NPs or emulsions of nanoscale dimensions. Dimensions of NMs and NPs selected nanofertilizers in the above five situations are usually in the range of 0.2 to 100 nm (nanometer).

Materials currently selected for NMs to generate nanofertilizers are either inorganic or organic in nature. Examples of inorganic NMs are nanoclays (such as modified montmorillonite nanocompounds), carbon nanotubes, biochar, nanosilica, alumina-silicate NPs, and nanoporous zeolite. Examples of organic NMs are polyacrylamide, starch, cellulose, polycaprolactone, and polylactic acid, all are organic polymeric materials. Processing methods reported in the past for nanofertilizers' NMs production include examples of solvent evaporation, solgel processing, hydrothermal processing, chemical precipitation, spraying vaporization, conventional heating, wet oxidation, and anodization.

U.S. Pat. No. 8,911,526 discloses an invention of synthesizing a porous leucite at nanoscale to replace the polymeric fertilizer and zeolites with nanoleucite as NM for the application in the slow release nitrogen fertilizer. This invention is using hydrothermal method in anionic surfactant (sodium dodecyl sulfate) to generate NMs. The surfactant is used to increase the porosity of the nanoleucite. The cation exchange capacity (CEC) of the NM is increased by occluding salts, mainly calcium ammonium nitrate into the pores. This invention claimed that the production method could generate a nanofertilizer less expensive and less time-consuming than that of zeolite and polymer nanofertilizers.

U.S. Pat. No. 9,828,299 relates methods of making ketoesters into compositions of fertilizers. Ketoesters may be appropriately formulated with agrochemicals and are rendered into fertilizers in soluble or NPs phases. Ketoesters, preferably β-ketoesters, more preferably acetoacetate esters, and most preferably ethyl acetoacetate (EAA) are proposed for rendering micellar coordination complexes as nanofertilizers. Compounds selected for micellar complexation include primary, secondary, and micro-nutrients, as well as pesticides. Generation processes mentioned are stirring, agitation, or heat facilitating the formation of fertilizer products.

US Patent Publication No. 2018/0250646 proposes an invention of organic NPs obtained from microemulsions by solvent evaporation. Organic NPs can be processed from water insoluble polymers such as polylactic acid, cellulose acetate, methyl cellulose, hydroxylpropyl methyl cellulose, poly(lactic-co-glycolic acid), hydroxylpropyl cellulose phthalate, or water soluble polymers such as polyvinyl pyrrolidone, polyvinyl alcohol, carboxy methyl cellulose, hydroxy ethyl cellulose, polyethylene glycol, or non-crosslinked polymers. The particle sizes of NPs claimed are less than 30 nm.

Although nanofertilizers having the capabilities of increasing nutrient utilization efficiency, improving crop growth, yield, and quality, as well as reducing soil and water contaminations and greenhouse effects, some agri-nanotechnology researchers, however, have sounded a loud note of caution on the safe use. Concerns are potential toxicity associated with nanoscale materials to soil microorganisms, degradation into toxic compounds in soils, intake of nano-toxins into plants, cumulation of toxic or unusable NMs and NPs in plants. Effects of long-term exposure of fertilizer NPs and NMs to manufacturing and farming workers, long-term synchronization of nutrients availability to plants, and long-term environmental consequences are largely unknown. Some of the above negative effects may require extensive experiments and years of lengthy time periods to confirm and resolve.

SUMMARY OF THE INVENTION

In order to mitigate or eliminate the above negative effects of applying nanofertilizers, this invention suggests that: (1) the NMs selected for nanofertilizer should be useful and nontoxic to plants, soil microorganisms, and human, (2) appropriate nano-sizes should be selected to avoid plant intake, (3) NMs selected for carrying nutrients, if allowing intake by plants, should be themselves useful to plants such as NMs are also plant growth-stimulating-agents. Based on the above item (1) criterion, NMs such as nanoclays, carbon nanotubes, nanochar, polyacrylamide may not be useful by plant intake, and existence of these materials in plant tissues may have potential to cause side effects (such as polyacrylamide decomposes into toxic acrylamide) and should be avoided. The entry of NPs through the cell wall depends on the pore size of the cell wall, usually 5 to 20 nm. Therefore, if NPs uptake by plants are to be avoided, as suggested in criterion (2) above, larger NP sizes should be selected. If NMs are provided for the purposes of encapsulation or coating, minimum particle sizes selected should be in the range of 50 to 100 nm, to avoiding intake by plants yet small enough to maintain significant Cation Exchange Capacity (CEC) values. If NMs are provided for other purposes such as adsorption or complexation of nutrients or pesticides, particle sizes selected for NMs can be even larger than 100 nm. Based on criterion (3) above, NMs selected shall be either plant growth stimulants or themselves are plant nutrients. Besides the above three criteria, other factors such as cost-effective to produce, supply of NMs shall be abundant to generate large quantities of nanofertilizers for agricultural purposes. Objectives of this invention is to propose the best NMs and their processing method for nanofertilizers production to achieve the above mentioned criteria.

The objectives of the present invention are to provide high-rate physicochemical processes and equipment to generate oxidized cellulosic nanomaterials (NMs) for coordination of nutrients to form organomineral nanofertilizers, and for the coordination of pesticides and herbicides to generate slow-release pesticide/herbicide products. This invention relates to nanotechnological process and equipment to generate nanomaterials (NMs) and reactive oxygen species reaction processes and equipment to produce oxidized cellulosic NMs for coordination of nutrients and pesticides and herbicides to generate high quality organomineral nanofertilizers and pesticide/herbicide nanoparticles from natural organic materials. This invention also related to dissolution and reactive oxygen species reaction processes and equipment for coordination of nutrients and pesticides and herbicides to generate high quality organomineral fertilizers and pesticide/herbicide nanoparticles from organic waste materials.

BRIEF DESCRIPTION OF THE DRAWINGS

The invention will be described in more detail by way of example only, with reference to the accompanying drawings. The following drawings are provided.

DETAILED DESCRIPTION OF THE INVENTION

Figure 1:
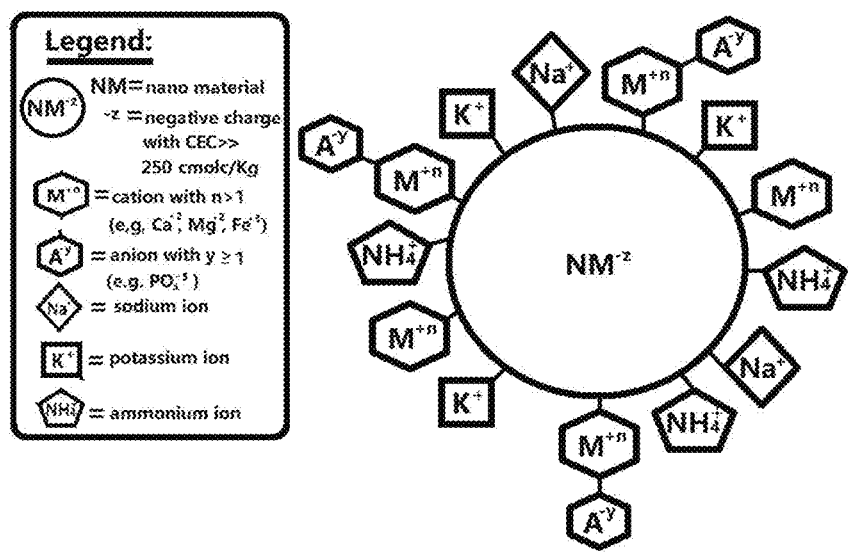
FIG. 1 is an illustration diagram showing the nutrient-NM complexation phenomenon as discussed in the present invention.

Organomineral nanofertilizers can significantly improve the nutrient utilization efficiency, increase crop growth, yield, and quality, as well as reduce soil and water contaminations and greenhouse effects. However, concerns are potential toxicity or degradation to toxic compounds associated with fertilizer nanomaterials (NMs) affecting soil microorganisms, plants, manufacturing and farming workers, and other long-term largely unknown environmental consequences. Mitigation or elimination of the above negative effects may require all of the followings: (1) selection of useful and nontoxic NMs to plants, soil microorganisms, and human for nanofertilizer, (2) selection of appropriate NMs' nano-sizes to avoid plant intake, and (3) selection of NMs, if allowing intake by plants, should be themselves utilizable by the plants such as NMs themselves are also plant growth-stimulating-agents and/or nutrients. Based on the above item (1) criterion, the subject invention selects the fully or nearly fully oxidized cellulosic materials as NMs for nanofertilizers. Since the pore sizes of the plant cell wall are usually 5 to 20 nm, in order to avoid further unknown negative effects as suggested in criterion (2) above, the minimum particle sizes of oxidized cellulosic NMs to be selected for the complexation of organic substances (such as humic acids), mineral nutrients and/or pesticides are greater than 50 nm but less than 1000 nm. Sizes of these NPs are small enough to maintain significant CEC values and Brownian effects but large enough to prevent uptake by plants. If NMs are provided for adsorption or complexation of nutrients or pesticides, particle sizes selected for NMs are more favorably in the range of 50 and 450 nm (traditionally, 450 nm is also selected for the separation of soluble and non-soluble phases), and most favorably in the range of 50 and 100 nm. Based on criterion (3) above, oxidized cellulosic NMs are plant growth stimulants or themselves are plant nutrients when nutrients are complexed and carried by the NMs. Besides the above three criteria, oxidized cellulosic NMs are cost-effective to produce, and supply of oxidized cellulosic NMs is abundant for the large quantity needs in the agricultural field. Utilization of oxidized cellulosic NMs in the above-mentioned particle sizes for nanofertilizers, and cost-effective processes of oxidized cellulosic NMs for the manufacturing of nanofertilizers are not reported in the published patent lists so far.

Sources of cellulosic materials may come from natural origin (such as lignite, leonardite, peat, wood, straw) and manmade organic type of solid wastes (such as agricultural wastes, animal wastes, municipal solid wastes, municipal sludge, etc.). Utilization of the above material sources to generate traditional composts or organic fertilizers are widely reported in the literature. Traditional main stream technologies to produce composts or organic fertilizers are biochemical processes to convert organic type of waste materials into fertilizers. These biochemical processes involve mainly two processes: "Biodegradation and Curing". In "Biodegradation" the Easily Biodegradable Organics such as protein, fats, and simple carbohydrates are decomposed by microorganisms partly using as energy and partly forming biomass. After "Biodegradation", the remaining materials in the organic type of wastes are biomass and Moderately Degradable Organics (mainly containing lignocellulosic materials, i.e., lignin, hemicelluloses, and celluloses). In "Curing" process the biomass is gradually eliminated due to no food available for the surviving microorganisms. After "curing" process the remaining materials are mainly lignocellulosic materials, which become the backbone of the traditional organic fertilizers. When the lignocelluloses are oxidized, humic substances formed. Hemicelluloses are among the lignocellulosic substances which usually oxidized more easily than lignin and celluloses. Among the backbone materials of organic fertilizers, celluloses are the most important ingredients which behave the major functions of organic fertilizers. These major functions include: (1) high water absorption capability, (2) high nutrient retention capability, (3) soil particle attenuation capability, (4) soil thermal insulation capability, (5) soil air transmission capability, and (6) soil water transmission capability. When organic fertilizers contain oxidized lignocellulosic materials, an additional function will appear, i.e., (7) providing stimulating agents for plant growing. Compounds derived from the oxidized lignocelluloses contain mainly humic substances, including humin, humic acids, and fulvic acids which are strong complexation agents and plant growing-stimulating-agents. Therefore, oxidized cellulosic materials will possess very high capabilities of all of the above seven functions comparing to that of traditional organic fertilizers. Utilization of oxidized cellulosic NMs, or cellulosic NMs complexed with humic substances for carrying nutrients in nanofertilizers is a much better way of fertilizer application in agriculture fields.

Most of the natural cellulosic material sources as mentioned above contain very small percentage of or without the existence of easily biodegradable organics. These types of natural cellulosic materials, especially lignite, leonardite, and peat, do not require biodegradation and curing processes for the generation of oxidized cellulosic NMs due to absence of easily biodegradable organics.

In the following sections the principles, major manufacturing processes, objectives, and major equipment to be applied for the generation of nanofertilizers by using the oxidized cellulosic NMs as the backbone materials for organomineral nutrients and pesticides are described.

1. Basic Principles, Operational Procedures and Objectives

Oxidized cellulosic NMs proposed in this invention are defined as oxidized nanoparticles (NPs) of lignocellulosic materials which a great portion of the celluloses are exposed, or pure celluloses NPs are treated by oxidation, or the above said lignocellulosic and cellulosic NPs are coordinated (surface treated) with humic substances. The particle sizes of the proposed oxidized cellulosic NMs used for nanofertilizers are in the range of 50 to 1000 nm. Sizes of these NPs are small enough to maintain significant Cation Exchange Capacity (CEC) values and Brownian effects. If NMs are provided for adsorption or complexation of nutrients or pesticides, particle sizes selected for NMs are more favorably in the range of 50 and 450 nm, and most favorably in the range of 50 and 100 nm. Due to the organic nature of the NMs to carry mostly inorganic nutrients, the fertilizer products can be classified as organomineral nanofertilizers.

Because of the nano-size nature and the existence of humic substances, the surface of the oxidized cellulosic NMs possesses with negative charges and with highly adsorption and complexation capability. There are at least four reactions can occur on the surface of oxidized cellulosic NMs: ionic attraction (by electric force), ion exchange, adsorption/absorption, and complexation. The negative charges of the oxidized cellulosic NMs are very favorable for the attachment of plant nutrients which are mostly existing as cationic species in solution, as illustrated in FIG. 1. Among the macronutrients (i.e., nitrogen, phosphorus, and potassium nutrients), secondary nutrients (i.e., calcium, magnesium, and sulfur nutrients), and micronutrients (such as iron, manganese, boron, copper, zinc, molybdenum, and chloride) only very few species are negatively charged, such as phosphate, sulfate, and chloride ions (shown as $A^{-y}$ in FIG. 1). These negative ions can be attracted by the cations (with charge more than 1 as shown as $M^{+n}$ in FIG. 1), which are already attached to NMs. The CEC of the oxidized cellulosic NMs are usually greater than 250 cmolc/Kg when sizes of NMs are less than 1000 nm. When sizes of NMs reduced below 450 nm the CEC values of NMs will increase significantly. The CEC value can far exceed 500 cmolc/Kg when NMs are below 100 nm with well exposed and loosen oxidized celluloses in the NMs.

Due to the existence of humic substances on the NMs' surface the previous mentioned plant nutrients and pesticides also can be attached to the NMs through complexation and ion exchange effects. Wide varieties of functional groups, such as carboxyl (—COOH), phenol (—OH), hydroxyl (—OH), ketone (—C═O), ester (O═C—O—R), ether (—C—O—C—), and amine (—NH$_2$, —NH, —N) are associated with humic substances which can attract cations through ion exchanges and also can coordinate nutrients and/or pesticides through complexation reactions. The nano-size nature of oxidized cellulosic NMs can also adsorb/absorb chemical species through active surface characteristics and large moisture retention capability.

2. Processes and Equipment Involved in the Overall System

Figure 2:
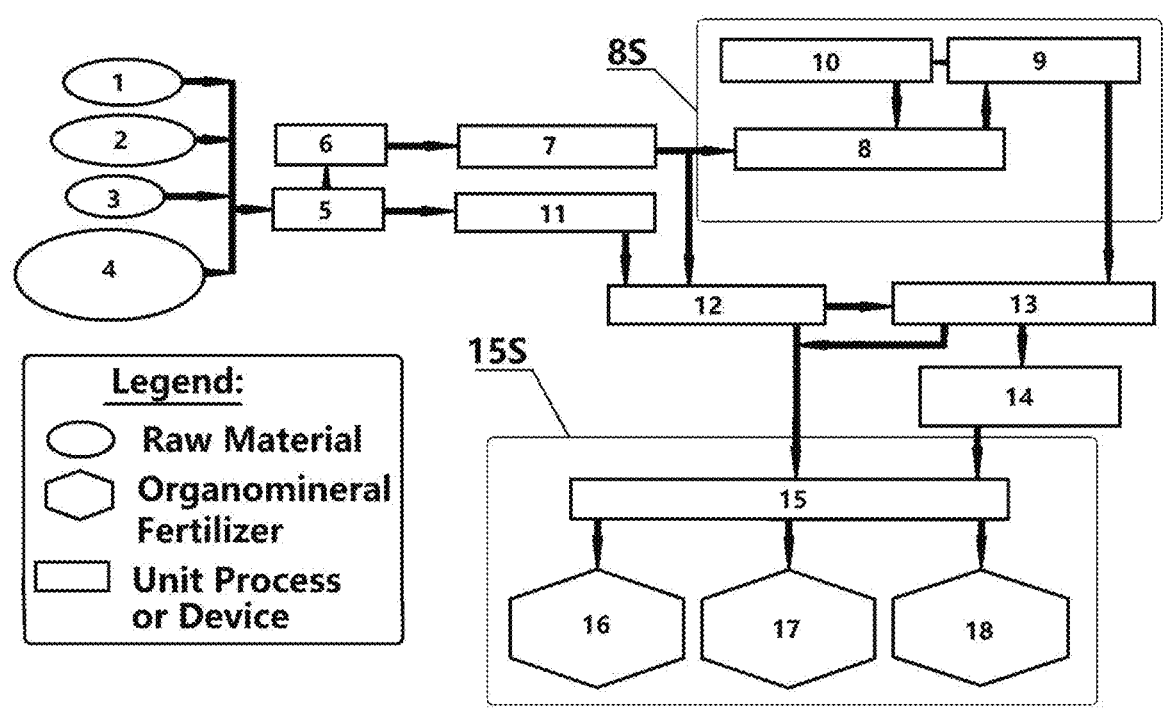
FIG. 2 is a block flow diagram (BFD) showing the major operation processes and reactors in the present invention.

The operational methods/processes and associated equipment for each unit process to finally generate oxidized cellulosic NMs and organomineral nanofertilizers are shown in FIG. 2. Lignite and/or leonardite (indicated as 1 in FIG. 2), wood and/or straw 2, peat 3, and pre-treated (to remove impurities) organic type of solid wastes 4 are processed by a shredding unit process 5 to reduce the particle sizes to around 2 mm sizes. Sizes of these shredded materials can be further reduced by a grinding unit process 6 to equal or less than 100 mesh (i.e., 0.15 mm) with a screen device attached to the grinder for size control. These grinded materials are stored in an equalization tank 7 preparing for the NPs generation by a NPs processing system 8S, as indicated in FIG. 2. If the input materials, such as pre-treated solid wastes, are containing significant amount of easily biodegradable organics the shredded materials can be stored in an equalization tank 11 preparing for the dissolution and wet thermal cracking operation 12 by a dissolution reactor. The moisture contents of the input materials are adjusted to 80 to 90% depending on the pumpable and mixable characteristics of the input materials in both equalization tanks 7 and 11. Details of the dissolution reactor will be further described later in this document and illustrated by FIG. 3. The above-mentioned shredder, grinder, and devices used for NPs processing system 8S are commercially available. The NPs processing system 8S includes a NPs processing device 8, an equalization tank 9, and a recirculation tank 10, as shown in FIG. 2. This NPs Processing system 8S is provided for input materials which do not require removing of easily biodegradable organics, such as lignite and leonardite input materials. Due to the needs for cost-effectiveness and fast processing speed, as well as nature of the input materials, the NPs processing device 8 selected is based on principles of synchronized oscillation and particle collision as will be further discussed latter in this document. After NPs processing device 8, the processed materials are stored in an equalization tank 9. If particle sizes are still not in the selected range, the processed materials are pumped to a recirculation tank 10 for re-processing.

Undesirable chemical compounds (such as easily biodegradable organics) and trace toxic substances (such as toxic organics or heavy metals in the input solid wastes) for the manufacturing of fertilizers can be solubilized in a dissolution reactor by dissolution processing 12, as will be further explained later in this document. These undesirable compounds can be decomposed and/or oxidized through the ROS processing 13 by a ROS Processing Reactor. ROS Processing Reactor can be used for oxidation of either the undissolved lignocellulosic materials from the dissolution reactor and NPs from the NPs processing system 8S. ROS Processing Reactor is also used to oxidize/decompose dissolved easily biodegradable organics from the dissolution reactor. Details of the functions of ROS Processing 13 are further discussed later in this document.

Processed materials from the dissolution reactor or the ROS processing reactor can then be treated by complexation/ion attraction/ion exchange/adsorption/absorption reactions in the product refining system 15S. Macronutrients, secondary nutrients, and micronutrients can be selected at in any combinations and coordinated in the product refining system 15S. The product refining system 15S includes multi-types of coordination reactors, for the generation of different types of fertilizer products, as will be further discussed later in this document. Different fertilizer product types may cover solid organomineral fertilizers 16, liquid organomineral fertilizers 17, and organomineral nanofertilizers 18 at different NP size ranges. When necessary, a liquid phase activation reaction 14 can be added to the processes to further loosen the lignocellulosic NMs to enhance the seven beneficial functions as discussed above. A traditional steam explosion device can be used for this purpose.

3. Principle and Equipment of the NPs Processing System

The NPs processing system 8S (shown in FIG. 2) and its associated devices are commercially available as mentioned above. Due to advantages of cost-effectiveness and fast processing speed, and suitability of the method for the size reduction of the lignocellulosic materials, the NPs processing system 8S is selected for this invention. The overall NPs processing system 8S includes an NPs processing device 8 which contains a fluid oscillator with multiple synchronized oscillation channels, a collision chamber, and an ultra-high-pressure pump. An equalization tank 9, and a recirculation tank 10 are provided in the NPs processing system 8S. The fluid with grinded particles (≤100 mesh) from the equalization tank 7 are pressurized to 100 to 200 Kg/cm$^2$, by the ultra-high-pressure pump associated with the NPs processing device 8. The pressure requirement is depending on the need for the desired reduced particle size levels (such as for ±100 nm NPs processing, pressure requirement is about 150 Kg/cm$^2$) adjusted by the ultra-high pressurized pump. This pressurized fluid is then pass through multiple synchronized oscillation channels in the NPs processing device 8 for size reduction. Fluid jets from the multi-oscillation channels are injected into the center of the collision chamber of the NPs processing device 8 for further size reduction. The mixed flow jets are then combined and flow to the equalization tank 9. Processing conditions are pre-tested and pre-adjusted by particle size measurements. This invention selected the fluid oscillation/collision method due to the special characteristics of the lignocellulosic materials which can be easily size adjusted by the selected method, besides the other advantages discussed above.

4. Principles and Equipment Design of the Dissolution Reactor

Figure 3:
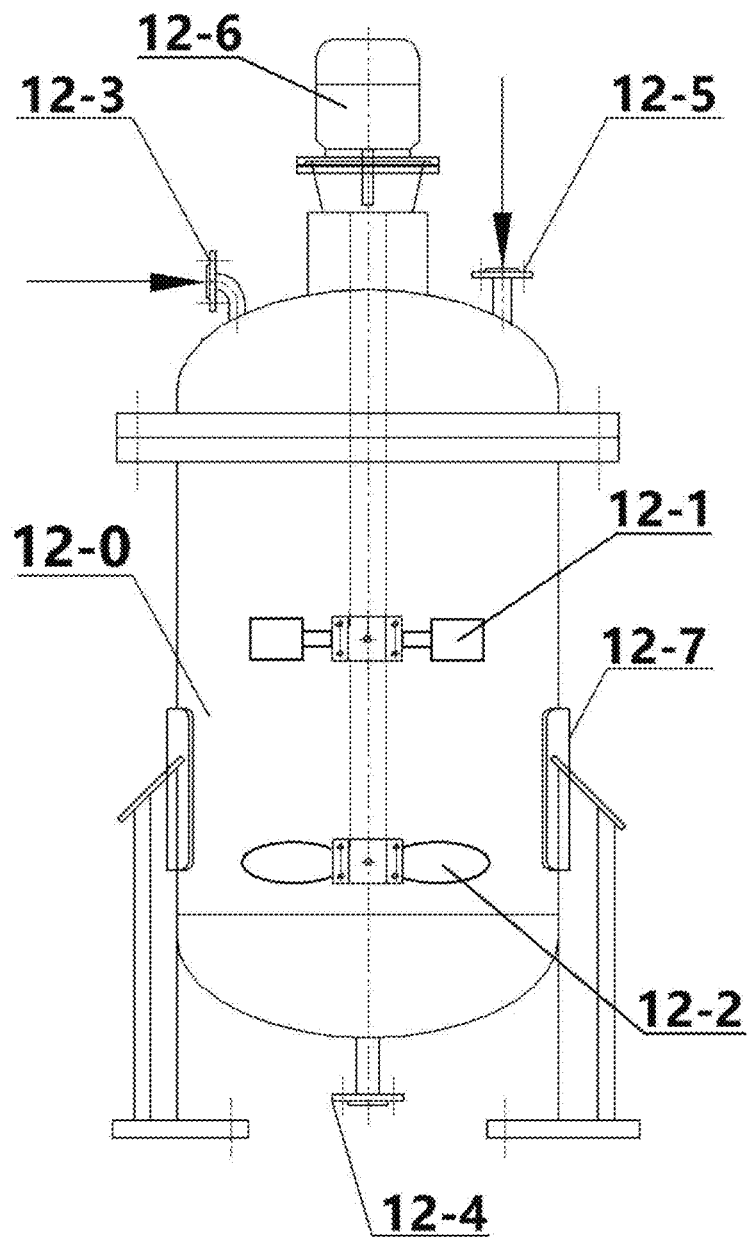
FIG. 3 is a structure diagram showing a profile of the Dissolution Reactor in one embodiment of the present invention.

Dissolution and wet thermal cracking operations (indicated as 12 in FIG. 2) are carried out by a dissolution reactor 12-0, as shown in FIG. 3. The dissolution reactor is a pressurized reactor which pressure is the saturated steam pressure corresponding to the water temperature in the Reactor. Processing of the moisture adjusted materials by dissolution reactions is necessary when the amount of easily biodegradable organics in the shredded materials are significant and need to be removed similar to that of the conventional curing in compost processing.

The temperature in the dissolution reactor 12-0 is adjusted to approximately 140 to 180° C. by a conventional heater, or by a heat exchanger to recover heat produced by the ROS processing reactor 13-1 (to be discussed in FIGS. 4A to 4G later). Multiple functions/reactions are involved in the dissolution reactor 12-0, such as hydrolysis/solubilization reactions, thermal cracking, organic radicals generation, organic radicals chain reactions, thermal loosening of lignocellulose fibers, sterilization of pathogens in organic wastes (if these wastes are used as input materials). Among the above mentioned reactions, the solubilization function is very important for the dissolution reactor 12-0 by which the easily biodegradable organics can be solubilized and subsequently decomposed in the following ROS processing reactor 13-1. In years of bench and pilot tests by the Inventor, it was found that the soluble organics species of the easily biodegradable organics can be easily formed by the subject dissolution reactor design. Among the easily biodegradable organics, proteins will form mainly soluble amino acids, oligopeptides, carbohydrate side chains from glycoproteins, racemized proteins, etc. by the thermal hydrolysis reactions. Our tests have found that most of the proteins can be hydrolyzed at temperatures above 120° C., majority of protein contents can be hydrolyzed when temperature reaches 180° C., and almost all proteins are hydrolyzed at temperature reaching 230° C. As for fats in the incoming materials, portion of complex fats will liquefy at room temperature, and at temperature beyond 80° C. most fats can be liquidized. When temperature reaching 180° C. majority of complex fats can be hydrolyzed into fatty acids and simple fats. As for the carbohydrates in the incoming materials, hydrolysis in the dissolution reactor 12-0 results in hydrolyzed glycogen (major glucose polymers from animal wastes), hydrolyzed starch (major glucose polymers from plant wastes), and simple sugars (such as glucose, galactose, mannose), etc. According to rough estimates, depends on types of input waste materials, approximately 55 to 65% of carbohydrates in food wastes can be hydrolyzed when temperature reaching 140° C., 25 to 35% of carbohydrates in wastes can be hydrolyzed reaching 140° C. to 230° C., and only about less than 10% carbohydrates need to be hydrolyzed at temperature beyond 230° C. Time needed for hydrolysis will depend on temperature, concentration, pH, particle sizes, etc. For most input materials discussed above, periods required for dissolution are from minutes to about 2 hours, when particle size is less than 2 mm and temperature within 140 to 180° C. However, the hydrolysis time can be reduced with the aid from acidic hydrolysis. To avoid over hydrolysis to reduce the production amount of cellulosic materials, appropriate temperature range selected is 140 to 180° C. In this temperature range hemicelluloses and a small portion of lignin of the lignocellulosic materials can also be hydrolyzed. Experiments found that cellulosic materials can be significantly hydrolyzed only when the temperature is higher than 250° C.

In the dissolution reactor 12-0 through the thermal chemical reactions the organic free radicals can be generated without the existence of oxygen. Reactions by thermal cracking can be shown as:

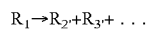

This phenomenon also can aid the breakdown of the particle sizes and enhance dissolution effects. The formed organic radicals also have the capability to initiate chain reactions to further breakdown and solubilize more compounds.

As shown in FIG. 3, the incoming materials from equalization tanks 7 and/or 11 (refer to FIG. 2), can be input into the dissolution reactor 12-0 through opening 12-3. The input materials are mixed in the tank to promote reactions by two types of mixers, the radical mixer (turbine type) 12-1 and axial mixer (propeller type) 12-2. The mixers are powered by a motor 12-6. Additive(s) can be added through opening 12-5 when necessary. The reactor is hold by a steel structure 12-7. Output materials can exit the reactor through opening 12-4. Inner materials used for the manufacturing of the reactor is titanium metal. The outer material used for the reactor can be carbon steel to reduce costs and increase thermal conductivity.

5. Principles and Equipment Design of the ROS Processing Reactors

After reactions proceeded in the dissolution reactor 12-0 discussed above, the treated materials are then pumped to the ROS processing reactor 13-1, as shown in FIGS. 2 and 4. The ROS processing reactor 13-1 is provided in this invention for multiple objectives. Two most important objectives are to oxidize/decompose easily biodegradable organics and generation of humic and fulvic acids. Other objectives such as further loosening of lignocelluloses (so more celluloses can be exposed), destruction of toxic organic compounds, sterilization of pathogens, release of nutrients from input materials, and dissolution of toxic heavy metals (for subsequent removal when necessary). The generation of ROS is initiated by DO, which will subsequently generate ROS compounds such as hydroxyl radical (OH.), hydrogen peroxide ($H_2O_2$), Super Oxygen Anion ($O_2.^-$), Peroxyl radical or Hydrogen Peroxide Radical (HOO.), and peroxyl anion (HOO), to be further delineated in this document.

Due to the rapid reaction characteristics of the ROS, maintenance of high temperature in the ROS processing reactor 13-1 is usually not required although high temperature can expedite the oxidation reactions. Temperature range for ROS processing can be from room temperature to as high as 200° C. However, maintenance of elevated pressure of the ROS processing reactor 13-1 is advantageous for the increase of soluble concentrations of some oxidants so reactions can proceed faster and more complete. Theoretically there is no upper limits of pressure shall be maintained in the ROS processing reactor 13-1, but high pressure tends to increase the cost of reactor. In this invention the pressure is kept at the range of 3 to 4 MPa, so dissolved oxygen (DO) levels can be maintained in the range of 300 to 500 ppm. DO level in the room temperature and atmospheric pressure is only about 8 ppm which is usually insufficient for the oxidation of the soluble easily biodegradable organics and generation of enough ROS for the generation of humic substances. The above-mentioned pressure range can be maintained by the extra external need of oxygen supply, through the air/oxygen input opening 13-3. Extra amount of oxygen need for the oxidation/decomposition of easily biodegradable organics is usually about ¼ of the total oxygen demand in the ROS processing reactor 13-1 as shown in FIG. 4A.

Series of reactions occur in the ROS processing reactor 13-1. These reactions are initiated from the cathode zone where multiple layers of circular shape of net-type cathodes 13-15 are provided, as shown in FIGS. 4A and 4B. The cathode zone is a cylindrical shape located in the center of the reactor as shown in FIGS. 4A and 4B. This cylindrical zone is formed by a specially designed carbon steel cylinder 13-16 coated by ferric phosphate as a catalyst material. Multiple jets 13-17 are arranged near the top of the cylinder to create turbulent flow and cavitation effects for the circulation of fluid in the reactor. This cylindrical material is connected to outside annular space where multilayers of net-type catalyst (made of the same steel carbon coated by ferric phosphate) are located as shown as 13-27 in FIGS. 4A and 4B. The net-type cathodes 13-15 are connected to a titanium metal rod 13-13 to form a cathodic system in the reactor. An axial type propeller 13-11 powered by a motor 13-10 and connected by a shaft 13-31 is arranged near the bottom of the cathode zone to push the flow upward into the cathode zone. This propeller mixer 13-11 can also be arranged on top of the cathode zone to suck up the flow. The multiple net-type anodes 13-14 made of titanium metal are connected to a titanium rod 13-12 to form an anodic system. The anodic system (with titanium metal) is coated with titanium dioxide semiconductor material. Insulation and sealing material is provided to segregate the cathode and anode systems from the reactor body and catalyst nets, as shown by 13-24 and 13-25 in FIGS. 4A, 4B, 4C, 4F, and 4G. Details of the sealing, screw tightening-insulation design are further illustrated in FIGS. 4F and 4G, where 13-33, 13-34 show titanium plates, 13-35 represents screw, and 13-37, 13-38 denote titanium metal rods designed for holding the electrodes. Electrode rods 13-12 and 13-13 are connected to the power source by wires 13-36, as shown in FIGS. 4F and 4G.

Figure 4A:
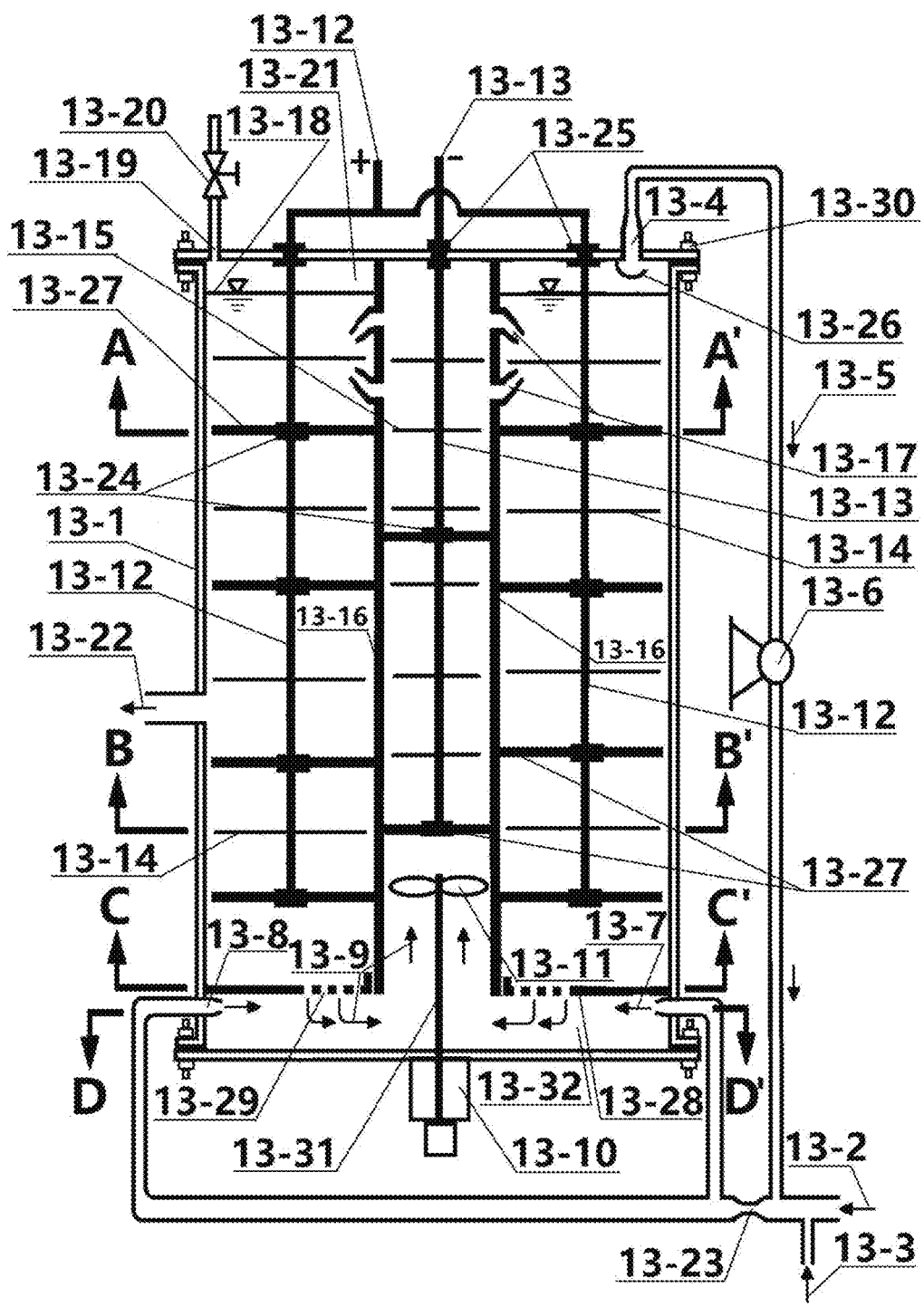
FIG. 4A is a structure diagram showing a cross-sectional view of the ROS Processing Reactor in one embodiment of the present invention.
Figure 4B:
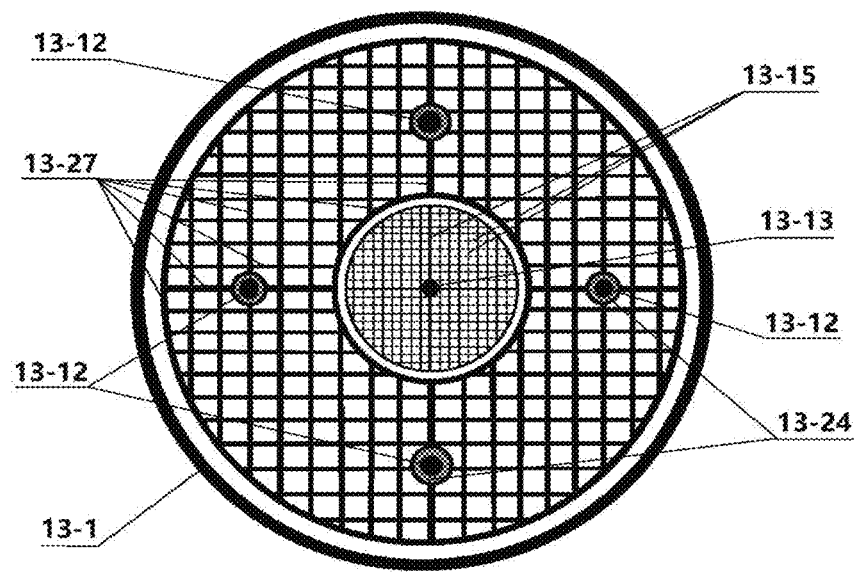
FIG. 4B shows the view of cross-section along A-A' as marked in FIG. 4A.
Figure 4C:
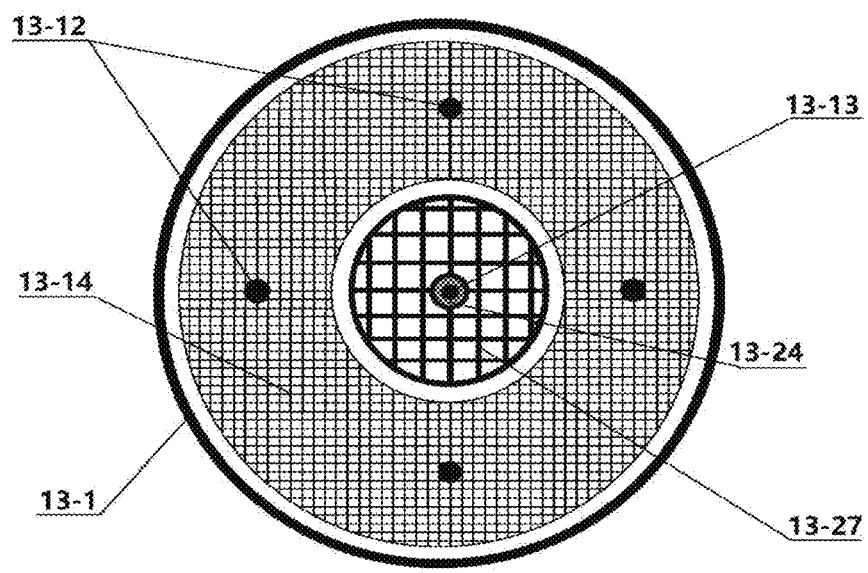
FIG. 4C shows the view of cross-section along B-B' as marked in FIG. 4A.
Figure 4D:
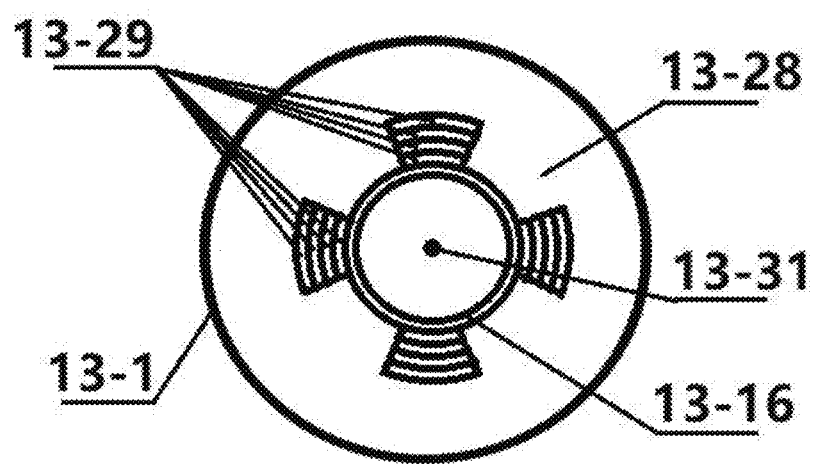
FIG. 4D shows the view of cross-section along C-C' as marked in FIG. 4A.
Figure 4E:
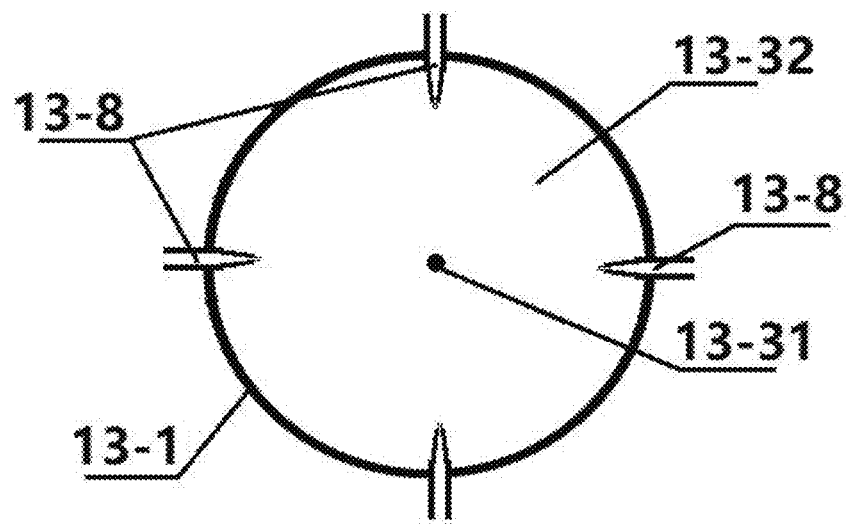
FIG. 4E shows the view of cross-section along D-D' as marked in FIG. 4A.
Figure 4F:
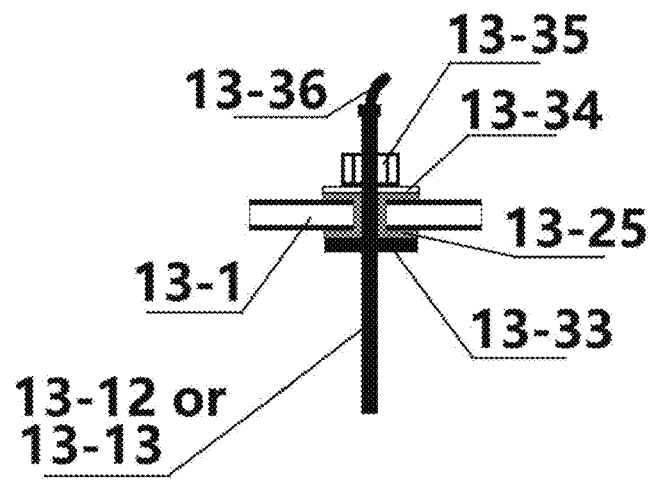
FIG. 4F shows the details of the structure at the location marked as 13-25 in FIG. 4A.
Figure 4G:
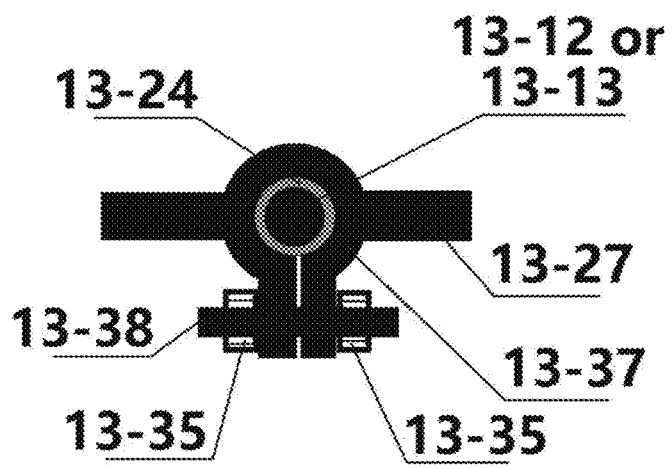
FIG. 4G shows the details of the structure at the location marked as 13-24 in FIGS. 4A, 4B, and 4C.

As shown in FIG. 4A, a small amount (usually about ¼ of the total oxygen demand) of pressurized air or oxygen is injected into the cathode zone of the ROS reactor 13-1 through an air input opening 13-3. The input material to the ROS reactor 13-1 from the dissolution reactor 12-0 is through opening 13-2. The air/steam formed in the space 13-21 can be removed through opening 13-19 controlled by valve 13-20 when necessary. The air/steam formed in the top space 13-21 above the fluid surface 13-18 of the ROS reactor 13-1 is pumped through opening 13-4, which is protected by a cup-shape opening 13-26. This recirculated steam is pumped by a pump 13-6, according to the flow direction 13-5 and mixing with the other input materials and external air/oxygen as discussed above and then pass through a Venturi device 13-23 to enhance the mixing and DO levels. The mixed stream then split into multiple input jets 13-8 as shown in FIGS. 4A and 4E to enter the ROS reactor 13-1 shown as 13-7 turbulent streams. The discharge nozzles of multiple input jets 13-8 can form a cavitation of nanobubbles by hydrodynamic cavitation in a low-pressure zone. The injected materials again are mixing with the recirculated materials already in the reactor, through openings 13-29 and mixed in space 13-32 in the reactor to form mixture 13-9. The space 13-32 is formed by the annular shape of catalyst plate 13-28. The treated fluid materials can exit the reactor through opening 13-22. The ROS reactor 13-1 is a cylindrical shape container with top and bottom removable plates holden by screws 13-30. Inner materials used for the construction of the ROS reactor 13-1 is titanium metal which is welded to the outer carbon steel material to reduce costs, increase strength and thermal conductivity.

In the cathode zone of the subject design, major ROS compounds are generated as explained below. ROS generation starts from the biradical nature of DO which has a very strong capability to capture electrons from the cathode nets 13-15 and electrons in the fluid. High DO levels can be produced from the anode nets 13-14 and input stream 13-7. Super Oxygen Anion ($O_2.^-$), as expressed by the formula below can be formed. The wire net design used for cathodes, so electron can be easily released and captured by DO, which also can prevent or reduce the chance of forming hydrogen gas in the cathode zone.

$$O_2 + e^- \rightarrow O_2{\cdot}^- \quad (1)$$

After that a series of rapid reactions follows:

$$O_2{\cdot}^- + H^+ \rightarrow HOO{\cdot} \quad (2)$$

$$HOO{\cdot} + e^- \rightarrow HOO^- \quad (3)$$

$$HOO^- + H^+ \rightarrow H_2O_2 \quad (4)$$

When hydrogen peroxide ($H_2O_2$) is formed, three types of reactions may occur to form hydroxyl radical (OH.), which is the strongest oxygen containing oxidant in the nature:

$$H_2O_2 + e^- \rightarrow OH^- + OH{\cdot} \quad (5)$$

$$H_2O_2 \rightarrow 2OH{\cdot} \quad (6)$$

$$H_2O_2 + Fe^{2+} + H^+ \rightarrow Fe^{3+} + OH{\cdot} + H_2O \quad (7)$$

The above Equation (7) is the well-known Fenton Reaction which will occur when catalyst such as in this case $Fe^{2+}/Fe^{3+}$ are present, which is provided as iron phosphate explained above. Since $e^-$ can be supplied from the cathodic system continuously by the design, and $Fe^{2+}$ can be formed as shown below:

$$Fe^{3+} + e^- \rightarrow Fe^{2+} \quad (8)$$

Therefore, Reaction (7) shall continue when catalyst is available. The ROS compounds as shown above will mainly include hydroxyl radical (OH.), hydrogen peroxide ($H_2O_2$), Super Oxygen Anion ($O_2{\cdot}^-$), Peroxyl radical or Hydrogen Peroxide Radical (HOO.), and peroxyl ion ($HOO^-$). Among them, hydroxyl radical and hydrogen peroxide will be the major ROS oxidants in the subject system. Due to short-life of hydroxyl radical, the fluid in the ROS reactor 13-1 is circulated at a fast speed to promote the oxidation reactions. It is also known that lignocellulosic materials are very difficult to oxidize by weak oxidants such as DO, ROS are thus provided in the subject invention for conversion of lignocellulosic materials into humic substances on the surface and within the loosen lignocellulosic particles. Particle sizes of the lignocellulosic materials are reduced to smaller dimensions in this invention, such as nano-sizes to enhance the oxidation reactions.

In the anode zone of the subject design, DO, hydroxyl radical, organic radicals, and electrons are formed if semiconductor materials are provided as anodes, as shown in the following:

(1) formation of electron holes on the surface of anodic nets to release electrons to initiate hydroxyl radicals generation:

$$TiO_2 + h\nu \rightarrow TiO_2(h+) + e^- \quad (9)$$

$$TiO_2(h+) + H_2O \rightarrow TiO_2 + OH{\cdot} + H^+ \quad (10)$$

(2) Oxidation of water:

$$H_2O \rightarrow \tfrac{1}{2}O_2 + 2H^+ + 2e^- \quad (11)$$

(3) Formation of organic radicals:

$$R \rightarrow R{\cdot} + e^- \quad (12)$$

The above hydroxyl and organic radicals formed can aid in breakdown of easily biodegradable organics and formation of humic substances. The oxygen formed by Equation (11) can supply about ¾ of the oxygen demand in the reactor system.

Titanium, graphite, reticulated carbon, Hastelloy are better cathode materials which can be used for the ROS processing reactor 13-1. For the anode electrode materials, the better choices will be Fe, Ti, metallic oxides, or any semiconductor materials. Fe electrode is relative inexpensive and may help to generate hydroxyl radicals, but itself will be sacrificed and requiring frequent replacement. Titanium anode if can be coated with titanium dioxide not only can assist forming hydroxyl radicals, the electron ejected from the electrode surface forming an electron hole also can assist attracting soluble organics to the hole to form organic radicals, and thus further breakdown organics.

6. Product Refining System for Organomineral Fertilizers

The product refining system 15S as shown in FIG. 2 is provided in this invention for refining different types of organomineral fertilizer products. Different fertilizer product types including solid organomineral fertilizers 16, liquid organomineral fertilizers 17, and organomineral nanofertilizers 18 at different NP size ranges can be produced. In the product refining system 15S, unit processes and/or equipment (indicated as 15 in FIG. 2) selected for this invention can be categorized and explained as follows:

(1) Refining of solid organomineral fertilizers 16:

In this category the input materials are from dissolution reactor 12-0 and ROS processing reactor 13-1 without going through the NPs processing system 8S. Particle sizes of the input materials may be beyond 1000 nm but much less than 2 mm in this case. The following equipment are usually involved for the refining of these fertilizer materials:

Dewatering device (Filter press is selected for its cost-effectiveness and suitability for achieving low moisture contents of the lignocellulo sic materials which ≤30% moisture contents can be obtained easily.);

Grinders (For size adjustment of the particles obtained from the dewatering device);

Coordination reactor (Mixing tanks with moisture adjusting function are provided for coordination of desired macronutrients, secondary nutrients, and/or micronutrients to the size adjusted fertilizer materials described above.); and Solid fertilizer bagging machine and bags.

The grinded products as discussed above also can be further processed by the NPs processing system 8S to generate wet nanoparticles for the generation of organomineral nanofertilizers 18, as discussed below.

(2) Refining of liquid organomineral fertilizers 17:

In this category the input materials are from the filtered (dewatered) liquid of the Category 1) above. In the subject invention if raw materials are from pretreated organic types of waste 4, pH levels of the mixed fluids from dissolution reactor 12-0 and ROS processing reactor 13-1 are reduced to the 4 to 5 range. Therefore, after dewatering to generate solid organomineral fertilizers 16 as discussed above, the humic acids are mostly associated with the solid portion of the products due to low pH nature. However, fulvic acids, which are more active and valuable fertilizer compounds, are soluble at the above mentioned pH range and will exist in the dewatered liquids. After the refining processes, the economic value of the liquid organomineral fertilizers 17 will be much higher than that of the solid organomineral fertilizers 16. The following equipment are usually involved for the refining of these fertilizer materials:

Product concentration device (Since the liquid fertilizers are from natural source materials or wastes which usually already contain suitable and adequate mineral ingredients. However, through the subject manufacturing operations, concentrations are diluted. For the purposes of shipping and concentrating of fulvic acids, product concentration is necessary. This operation is achieved by using the Mechanical Vapor Recompression, MVR, device.);

Liquid coordination reactor (Liquid mixing tanks are provided for coordination of desired macronutrients, secondary nutrients, and/or micronutrients to the levels needed, especially for countries where minimum liquid concentration standards are provided in regulations.); and Liquid organomineral fertilizer packaging machine and containers.

(3) Refining of organomineral nanofertilizers 18:

In this category the input materials are from the NPs processing system 8S and the ROS processing reactor 13-1 as shown in FIG. 2. Raw input materials of the natural origin are usually processed in this category. The following equipment are usually involved for the refining of these fertilizer materials:

Product concentration device (Since the NMs produced from the NPs processing system 8S are usually diluted by the NPs processing device 8, product concentration is needed. This operation is achieved by using the MVR device.);

Colloid coordination reactor (Colloid mixing tanks are provided for coordination of desired macronutrients, secondary nutrients, and/or micronutrients to the levels needed, especially for countries where minimum liquid concentration standards are provided in regulations.); and Organomineral nanofertilizer packaging machine and containers (Similar to the liquid organomineral fertilizer packaging machine and containers, as discussed above, can be used.)

Equipment mentioned in the above product refining system 15S all are commercially available. The above said processes and equipment also can be used for the particle coordination of other materials including pesticides, herbicides and other compounds which are useful for the agricultural purposes. In general, materials of nature origin such as lignite and/or leonardite 1, wood and/or straw 2 as mentioned above containing large quantity of lignocelluloses can be size reduced by the NPs processing system 8S before the dissolution processing 12 and ROS processing 13. However, organic types of waste which containing high levels of easily biodegradable organics should be treated by dissolution processing 12 and ROS processing 13 then processed by the NPs processing system 8S if size reduction to nano-scales is planned.

Principles, methods and major apparatus are described above to produce organomineral nanofertilizers and other types of solid and liquid organomineral fertilizers based on the strong complexation nature of oxidized cellulosic nanoparticles. Other types of compounds used in the agriculture fields including pesticides, herbicides also can be attached to the oxidized cellulosic nanoparticles to increase their efficiencies and reduce pollution potential. It will be apparent to one of ordinary skill in the art that many changes and modifications can be made thereto without departing from the spirit or scope of the appended claims:

I claim:

1. A method for making a nanofertilizer, comprising
   (1) shredding an input raw material to less than 2 mm in size to obtain a shredded material,
   (2) grinding the shredded material to a size of equal or less than 0.15 mm to obtain a grinded material,
   (3) equalizing and adjusting the grinded material to have a moisture content of 80% to 90% to obtain a moisture adjusted material,
   (4) processing the moisture adjusted material to have a size in a range of between 50 nm and 1000 nm by a nanoparticle processing system, wherein the processed moisture adjusted material has no significant amount of biodegradable organics,
   (5) processing the moisture adjusted material by dissolution and thermal cracking reaction, when the input raw material contain significant amount of biodegradable organics,
   (6) equalizing and refining the processed moisture adjusted material by recirculating and repeat treating the processed moisture adjusted materials from step (5) by the nanoparticle processing system,
   (7) processing the processed materials of steps (5) and (6) by reactive oxygen species to generate oxidized cellulosic nanomaterial, wherein the reactive oxygen species selected from the group consisting of hydroxyl radical, hydrogen peroxide compounds, and a combination of hydroxyl radical and hydrogen peroxide compounds,
   (8) treating the oxidized cellulosic nanomaterial by a process that is selected from the group consisting of complexation, ion attraction, ion exchange, adsorption, absorption, and a combination thereof, in a product refining system to incorporate macronutrients, secondary nutrients, micronutrients, pesticides, herbicides, or combinations thereof on a surface of or into the oxidized cellulosic nanoparticles to generate products that are selected from the group consisting of a solid organomineral fertilizer, a liquid organomineral fertilizers, an organomineral nanofertilizer, pesticide nanoparticles, herbicide nanoparticles, and a combination thereof, in different particle size ranges, and
   (9) optionally loosening the oxidized cellulosic nanomaterial from step (7) prior to (8) by a liquid phase activation reaction to enhance beneficial function of fertilizer products that are nanoparticle fertilizers and pesticides or herbicides products.

2. The method for making the nanofertilizer as described in claim 1, wherein the input raw material comprises an input fluid material, and step (4) of the method further comprises
   reducing particle size of the input fluid material by a high pressure multiple fluid synchronized oscillating and particle collision operation in the nanoparticle processing system,
   checking the particle size, and
   recirculating the high pressure multiple fluid synchronized oscillating and particle collision operation,
   wherein the input fluid material is pressurized to 100 to 200 Kg/cm$^2$, and the particle sizes are processed to the range of from 50 nm to 1000 nm.

3. The method for making the nanofertilizer as described in claim 1, wherein the dissolution and the thermal cracking reaction are conducted at a selected temperature in a range of 140° C. to 180° C., a pressure automatically formed at a saturated steam pressure at the selected temperature, an input raw material particle size of less than 2 mm, and a moisture adjusted to a range of 80% to 90%.

4. The method for making the nanofertilizer as described in claim 1, wherein the reactive oxygen species processing is conducted to oxidize or decompose biodegradable organics, generate humic and fulvic acids, loosen lignocelluloses, destruct toxic organic compounds, sterilize pathogens, release nutrients from input raw material, and dissolve toxic heavy metals, and
   the reactive oxygen species processing is initiated by reaction of oxygen with electrons supplied in a system in a temperature range from room temperature to 200° C., a pressure range from 3 MPa to 4 MPa, a dissolved oxygen level in a range of 300 to 500 ppm with about ¼ of a total oxygen demand in the processing from an external air or oxygen supply.

5. The method for making the nanofertilizer as described in claim 1, wherein product refining step (8) further comprises
(1) refining the solid organomineral fertilizer by dewatering, grinding, coordination reaction, and packaging;
(2) refining the liquid organomineral fertilizer by mechanical vapor recompression, coordination reactions, and packaging;
(3) refining the organomineral nanofertilizer by mechanical vapor recompression, coordination reactions, and packaging; and
(4) processing pesticides and herbicides by coordinating to the oxidized cellulosic nanomaterial.

6. The method for making the nanofertilizer as described in claim 1, wherein
the input raw material is shredded by shredders to less than 2 mm in size;
the shredded material from step (1) is grinded by a grinder to less than 0.15 mm in particle size;
the grinded material is adjusted by an equalization tank to 80% to 90% of moisture content before step (4);
the nanoparticle processing system used in step (4) further comprises an equipment of a synchronized fluid oscillator with a particle collision design, an ultra-high-pressure pump, an equalization tank, and a recirculation tank, and the nanoparticle processing system is used to process the grinded and moisture adjusted materials from step (3) to have the particle size in a range of between 50 nm and 1000 nm;
the shredded material from step (1) or the shredded and grinded material from step (2) from the input raw material containing significant amount of biodegradable organics are processed by dissolution reactors in step (5);
materials from step (5), step (6), or both are processed in a reactive oxygen species reactor to generate the oxidized cellulosic nanomaterial in step (7);
the oxidized cellulosic material from step (7) is further loosened and exposed in a liquid phase steam explosion device in step (9); and
the oxidized cellulosic nanomaterial from step (7) or (8) is treated in a product refining system to generate the nanoparticle fertilizers and pesticides or herbicides products in step (9).

7. The method for making the nanofertilizer according to claim 6, wherein the dissolution reactor comprises
a tank with outer carbon steel material welded with inner titanium material,
two types of mixers in the tank, the first type of the mixers being a turbine type radical mixer (12-1), and the second type of the mixers being a propeller type axial mixer (12-2) powered by a motor (12-6),
an input opening for receiving the input raw material,
an additive opening (12-5) for receiving additives, and
an exit opening for outputting treated material.

8. The method for making the nanofertilizer as described in claim 6, wherein the reactive oxygen species reactor is a cylindrical-shaped container with a top removable plate and a bottom removable plate and titanium inner material welded to an outer carbon steel material, with two electric zones of a cathode zone and an anode zone for providing multiple net-types electrodes, a vertical cylindrical-shaped catalyst device separating the two electric zones, and an air/steam recirculating system outside the reactor;
the cathode zone is located inside a catalyst cylinder for providing multiple layers of circular shaped net-type cathodes (13-15) and connecting to a titanium metal rod (13-13) to form a cathodic system, an axial type propeller (13-11) with a motor (13-10), and a connecting shaft (13-31) for circulating fluid;
the anode zone is located outside the catalyst cylinder for providing multiple layers of annular shapes net-type anodes (13-14) coated with titanium dioxide semiconductor material and connecting to multiple titanium metal rods (13-12) to form an anodic system;
the cylindrical-shaped catalyst device is located between the cathode zone and the anode zones and is constructed with carbon steel material coated with iron phosphate catalyst for providing the multiple circular net-shaped catalyst device inside the cylinder and multiple annular net-shaped catalyst device outside the cylinder; and
the air/steam recirculating system is located outside the reactor for withdrawing air/steam formed in the reactor through a top space (13-21) above a fluid surface (13-18) of the reactive oxygen species reactor (13-1) to recirculate the air/steam according to a flow direction (13-5) and mixing with other input materials and external air/oxygen, passing through a Venturi device (13-23), and splitting into multiple input jets (13-8) to enter the reactive oxygen species reactor (13-1) as turbulent streams (13-7) to mix with recirculated material in the reactor.

9. The method for making the nanofertilizer as described in claim 6, wherein the product refining system further comprises:
an equipment for refining the solid organomineral fertilizer comprising a filter-press dewatering machine, a grinder, a coordination reactor with additive mixing device, a nanoparticle processing system for further size reduction, and a solid organomineral fertilizer product bagging machine;
an equipment for refining the liquid organomineral fertilizer comprising a mechanical vapor recompression system, a coordination reactor with additive mixing device, and a liquid organomineral fertilizer packaging machine;
an equipment for refining the organomineral nanofertilizer comprising a mechanical vapor recompression system, a coordination reactor, and organomineral nanofertilizer packaging machine; and
an equipment for coordinating pesticides and herbicides to the oxidized cellulosic nanomaterial comprising a coordination reactor and a packaging machine,
wherein macronutrients, secondary nutrients, micronutrients, pesticides, and herbicides are coordinated to the oxidized cellulosic nanomaterial in the product refining system.

* * * * *